US006300122B1

(12) United States Patent
Cox

(10) Patent No.: US 6,300,122 B1
(45) Date of Patent: Oct. 9, 2001

(54) METHOD FOR APPLYING ENZYME TO NON-FINISHED CELLULOSIC-CONTAINING FABRICS TO IMPROVE APPEARANCE AND FEEL CHARACTERISTICS

(75) Inventor: Thomas C. Cox, Rock Hill, SC (US)

(73) Assignee: Genencor International, Palo Alto, CA (US)

( * ) Notice: Subject to any disclaimer, the term of this patent is extended or adjusted under 35 U.S.C. 154(b) by 0 days.

(21) Appl. No.: 08/191,046

(22) Filed: Feb. 3, 1994

Related U.S. Application Data

(63) Continuation-in-part of application No. 08/117,648, filed on Sep. 8, 1993, now Pat. No. 6,156,562, which is a continuation of application No. 07/810,962, filed on Dec. 20, 1991, now abandoned.

(51) Int. Cl.⁷ ...................................................... C12N 9/42
(52) U.S. Cl. ........................... 435/263; 435/209; 8/116.1; 26/1; 28/100
(58) Field of Search ................................... 435/263, 209; 8/116.1; 26/1; 28/100

(56) References Cited

U.S. PATENT DOCUMENTS

| 2,106,257 | 1/1938 | Schwartz | 252/2 |
|---|---|---|---|
| 3,627,688 | 12/1971 | McCarty et al. | 252/153 |
| 3,776,693 | 12/1973 | Smith et al. | 8/142 |
| 3,950,277 | 4/1976 | Stewart et al. | 252/541 |
| 4,443,355 | 4/1984 | Murata et al. | 252/174.12 |
| 4,479,881 | * 10/1984 | Tai | 252/8.8 |
| 4,489,455 | * 12/1984 | Spendel | 8/158 |
| 4,661,289 | 4/1987 | Parslow et al. | 252/547 |
| 4,738,682 | 4/1988 | Boegh et al. | 8/401 |
| 4,760,025 | 7/1988 | Estell et al. | 435/222 |
| 4,822,516 | 4/1989 | Suzuki et al. | 252/174.12 |
| 4,832,864 | 5/1989 | Olson | 252/174.12 |
| 4,912,056 | 3/1990 | Olson | 435/263 |
| 4,981,611 | 1/1991 | Kolattukudy et al. | 252/550 |
| 5,006,126 | 4/1991 | Olson et al. | 8/401 |
| 5,103,883 | 4/1992 | Viikari et al. | 144/342 |
| 5,120,463 | 6/1992 | Bjork et al. | 252/174.12 |
| 5,122,159 | 6/1992 | Olson et al. | 8/401 |
| 5,185,258 | 2/1993 | Caldwell et al. | 435/220 |
| 5,232,851 | 8/1993 | Cox et al. | 435/263 |

FOREIGN PATENT DOCUMENTS

| 265832 | 5/1988 | (EP) . |
|---|---|---|
| 269977 | 6/1988 | (EP) . |
| 1372034 | 10/1974 | (GB) . |
| 2094826 | 9/1982 | (GB) . |
| WO89/09259 | 10/1989 | (WO) . |

* cited by examiner

Primary Examiner—Leon B. Lankford, Jr.
(74) Attorney, Agent, or Firm—Burns, Doane, Swecker & Mathis LLP

(57) ABSTRACT

A more efficient method of improving the feel and appearance of cellulosic-containing fabric prior to finishing which method comprises contacting the fabric with a cellulase solution under pressure, and under conditions wherein the solution cascades across the fabric, and under conditions effective in improving the feel and appearance of the cellulosic-containing fabric.

21 Claims, No Drawings

METHOD FOR APPLYING ENZYME TO NON-FINISHED CELLULOSIC-CONTAINING FABRICS TO IMPROVE APPEARANCE AND FEEL CHARACTERISTICS

CROSS-REFERENCE TO RELATED APPLICATIONS

This application is a continuation-in-part of U.S. Ser. No. 08/117,648 filed Sep. 8, 1993 now U.S. Pat. No. 6,156,562 which, in turn is a continuation of U.S. Ser. No. 07/810,962 filed Dec. 20, 1991 now abandoned the disclosure of both of which are incorporated herein by reference in their entirety.

BACKGROUND OF THE INVENTION

1. Field of the Invention

The present invention is directed to methods for improving the feel and appearance characteristics of cellulosic-containing fabrics. In particular, the methods of the present invention are directed to applying a cellulase solution under pressure to cellulosic-containing fabric during the manufacturing process under conditions wherein the solution cascades over the fabric. When so conducted, the treated cellulosic-containing fabric has improved feel and appearance characteristics as compared to the fabric prior to treatment, which improvement is achieved in an efficient manner. Additionally, this process removes a portion of the immature cellulosic-containing fibers from the fabric which provides for further improvements in the quality of the so-treated fabric.

2. State of the Art

During or shortly after its manufacture, cellulosic-containing fabrics are generally treated in a manner which improves their appearance and accordingly their quality. One means of improving the appearance and luster of such fabrics is to treat the fabric with a caustic alkaline reagent, for example, sodium hydroxide, and the like. This process of treating fabric with a caustic is termed "mercerization" and provides beneficial results to the so-treated fabric including increased dye yield, and increased tensile strength, increased luster, and appearance. However, use of such caustic reagents raises handling problems and safety concerns.

The art, in general, also teaches the application of cellulase enzymes to cellulosic-containing fabric to enhance the feel and/or appearance of the fabric. Such applications are described, for example, by Cox et al., U.S. Pat. No. 5,232,851, which discloses methods for treating non-dyed and non-finished cotton woven fabrics with a cellulase solution with agitations and under conditions so as to produce a cascading effect of the solution over the fabric. When so treated, improvements in feel and appearance are achieved under more efficient conditions as compared to treatment of the fabric with agitation only. Other fabrics heretofore treated with cellulase solutions under agitation and cascading conditions include cotton knits and cotton denims.

Notwithstanding the advantages and improvements achieved by treating cellulosic-containing fabrics with a cellulase solution with agitation and under conditions so as to produce a cascading effect of the solution over the fabric, the processes described by Cox, et al., U.S. Pat. No. 5,232,851, and others nevertheless have reaction times which are undesirably long for an efficient manufacturing process. Moreover, while such processes reduce fabric strength loss as compared to processes which do not agitate and cascade the cellulase solution over the cotton-containing fabric, additional reductions in strength loss are desirable.

In any event, the above described methods of contacting cellulosic-containing fabrics during manufacture with a cellulase solution are contrasted with methods of cleaning fabrics with a laundry detergent composition containing cellulase because the cellulosic-containing fabrics employed in the methods described herein are treated during the manufacturing process, e.g., prior to application of a finish to the fabric.

In spite of the above described methods, there is a continuing need for methods to upgrade the quality of cellulosic-containing fabrics by treatment with a cellulase solution while reducing/minimizing the treatment reaction time, particularly during the manufacture of cotton woven fabric. Likewise, there is a need for methods to upgrade the quality of cellulosic-containing fabrics by treatment with a cellulase solution during the manufacturing process that are more efficient than the methods of merely cascading and/or agitation. It would be particularly desirable if such methods also resulted in fabrics having improved appearance and feel with minimal strength loss as compared to fabrics prior to treatment.

SUMMARY OF THE INVENTION

The present invention relates, in part, to the discovery of new methods for more efficiently improving the feel and appearance of cellulosic-containing fabrics during the manufacturing process. Substantial and unexpected improvements in the treatment time and in the reduction of strength loss of cellulosic-containing fabrics have been discovered by contacting the fabric with a cellulase solution under pressure wherein the cellulase solution cascades over the fabric.

When treated in the manner of the present invention, the cellulase exposure time required to achieve improved feel and appearance of the treated cellulosic-containing fabric is significantly reduced as compared to prior art cellulase treatment processes including methods using agitation/cascading but without pressure application as described by Cox, et al., U.S. Pat. No. 5,232,851. Because the fabric is exposed to the cellulase solution for significantly shorter periods than those previously used, strength loss in the fabric as a result of the cellulose treatment is reduced as compared to known cellulase exposure procedures previously used.

Accordingly, in one of its method aspects, the present invention is directed to a method for improving the feel and appearance of cellulosic-containing fabric prior to finishing of the fabric which method comprises contacting the fabric with a cellulase solution under pressure, and under conditions wherein the solution cascades across the fabric, and under conditions effective in improving the feel and appearance of the cellulosic-containing fabric.

DETAILED DESCRIPTION OF THE PREFERRED EMBODIMENTS

As noted above, the methods of this invention provide for cellulosic-containing fabric having the desired properties of improved feel and appearance with a significant reduction in the amount of treatment time with the cellulase solution. The reduction in treatment time results in reduced strength loss in the fabric and provides for a more efficient process. Prior to our discussing this invention in detail, the following terms will first be defined.

1. Definitions

The term "cellulosic-containing fabric" means fabrics made of pure cotton or cotton blends; when cotton blends are employed, the amount of cotton in the fabric should be at least about 40% by weight cotton; preferably, more than about 60% by weight cotton; and most preferably, more than about 75% by weight cotton. When employed as blends, the companion material employed in the fabric can include one or more non-cotton fibers including synthetic fibers such as polyamide fibers (for example, nylon 6 and nylon 66), acrylic fibers (for example, polyacrylonitrile fibers), and polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramid fibers. It is contemplated that regenerated cellulose, such as rayon, could be used as a substitute for cotton in the methods of this invention.

The term "finishing" as employed herein means the application of a sufficient amount of finish to the fabric so as to substantially prevent cellulolytic activity of the cellulase on the fabric. Finishes are generally applied at or near the end of the manufacturing process of the fabric for the purpose of enhancing the properties of the fabric, for example, softness, drapability, etc. Finishes useful for finishing a cellulosic-containing fabric are well known in the art and include resinous materials, such as melamine, glyoxalol, or ureaformaldehyde, as well as waxes, silicones, fluorochemicals and quaternaries. When so finished, the cellulosic-containing fabric is also substantially less reactive to cellulase.

The term "cellulase" as employed herein refers to a multi-enzyme system derived from a microorganism which acts on cellulose, especially crystalline forms of cellulose, and its derivatives to hydrolyze cellulose and give as primary products, glucose and cellobiose. Such cellulases are synthesized by a large number of microorganisms including fungi, actinomycetes, gliding bacteria (mycobacteria) and true bacteria. Some microorganisms capable of producing cellulases useful in the methods described herein are disclosed in British Patent No. 2,094,826A, the disclosure of which is incorporated herein by reference. Most cellulases generally have their optimum activity in the acidic or neutral pH range. On the other hand, alkaline cellulases, i.e., cellulases showing optimum activity in neutral or alkaline media, are also known in the art. Microorganisms producing alkaline cellulases are disclosed in U.S. Pat. No. 4,822,516, the disclosure of which is incorporated herein by reference. Other references disclosing alkaline cellulases are EPA Publication No. 269,977 and EPA Publication No. 265,832, the disclosures of which are also incorporated herein by reference.

Cellulase produced by a microorganism is sometimes referred to herein as a "cellulase system" to distinguish it from the classes and components of cellulase isolated therefrom. Such classes and components are well known in the art and include exo-cellobiohydrolase components ("CBH components"), endoglucanase components ("EG components"), and β-glucosidase components ("BG components").

The CBH components and EG components are known in the art to synergistically interact with each other to provide enhanced activity against cellulose. Thus, while a cellulase system derived from any microorganism can be employed herein, it may be preferable that the cellulase system contain at least one CBH component and at least one EG component so that enhanced cellulase activity is achieved.

On the other hand, in a further preferred embodiment, the cellulase employed may be enriched in endoglucanase components. See U.S. Ser. No. 07/770,049, filed on Oct. 4, 1991 by Ward et al. entitled "TRICHODERMA REESEI CONTAINING DELETED AND/OR ENRICHED CELLULASE AND OTHER ENZYME GENES AND CELLULASE COMPOSITIONS DERIVED THEREFROM", which is a continuation-in-part application of U.S. Ser. No. 07/593,919, both of which are incorporated herein by reference. Such EG enriched cellulases can also be achieved by purifying a cellulase system into its components and then recombining requisite amounts of components. See International Patent Application Publication No. WO8909259, which is incorporated herein by reference.

Fermentation procedures for culturing cellulolytic microorganisms for production of cellulase are known per se in the art. For example, cellulose systems can be produced either by solid or submerged culture, including batch, fed-batch and continuous-flow processes. The collection and purification of the cellulase systems from the fermentation broth can also be accomplished by procedures known per se in the art.

Preferred cellulases for use in this invention are those obtained from *Trichoderma longibrachiatum* (formerly named *Trichoderma reesei*), *Trichoderma koningii*, Pencillum sp., *Humicola insolens*, and the like. Certain cellulases are commercially available, i.e., "CELLUCLAST" (available from NOVO Industry, Copenhagen, Denmark), "RAPIDASE" (available from Gist Brocades, N.V., Delft, Holland), "CYTOLASE 123" (available from Genencor International, South San Francisco, California), "PRIMAFAST 100" cellulase (available from Genencor International, South San Francisco, Calif.), and the like. Other cellulases can be readily isolated by art recognized fermentation and isolation procedures.

The term "buffer" refers to art recognized acid/base reagents which stabilize the cellulase solution against undesired pH shifts during the cellulase treatment of the cotton woven fabric. In this regard, it is art recognized that cellulase activity is pH dependent. That is to say that a specific cellulase will exhibit cellulolytic activity within a defined pH range with optimal cellulolytic activity generally being found within a small portion of this defined range. The specific pH range for cellulolytic activity will vary with each cellulase. As noted above, while most cellulases will exhibit cellulolytic activity within an acidic to neutral pH profile, there are some cellulases which exhibit cellulolytic activity in an alkaline pH profile.

During cellulase treatment of the cellulosic-containing fabric, it is possible that the pH of the initial cellulase solution could be outside the range required for cellulase activity and that a buffer is required in order to adjust the pH of the solution. It is further possible for the pH to change during treatment of the cellulosic-containing fabric, for example, by the generation of a reaction product which alters the pH of the solution. In either event, the pH of the unbuffered cellulase solution could be outside the range required for cellulolytic activity. When this occurs, undesired reduction or cessation of cellulolytic activity in the cellulase solution occurs.

For example, if a cellulase having an acidic activity profile is employed in a neutral unbuffered aqueous solution, then the pH of the solution will result in lower cellulolytic activity and possibly in the cessation of cellulolytic activity. On the other hand, the use of a cellulase having a neutral or alkaline profile in a neutral unbuffered aqueous solution should initially provide cellulolytic activity.

In view of the above, the method of this invention provides that the pH of the cellulase solution is maintained within the range required for cellulolytic activity. One means for accomplishing this is by simply monitoring the pH of the system and adjusting the pH as required by the addition of either an acid or a base. However, in a preferred embodiment, the pH of the system is preferably maintained within the desired pH range by the use of a buffer in the cellulase solution. In general, an amount of buffer is employed which is sufficient so as to maintain the pH of the solution within the range wherein the employed cellulase exhibits activity while not enhancing the rate of strength loss of the treated fabric.

Insofar as different cellulases at different pH ranges exhibit cellulase activity, the specific buffer employed is selected in relationship to the specific cellulase employed. The buffer(s) selected for use with the cellulase employed can be readily determined by the skilled artisan taking into account the pH range and optimum for the cellulase employed as well as the pH of the cellulase solution. Preferably, the buffer employed is one which is compatible with the cellulase and which will maintain the pH of the cellulase solution within the pH range required for optimal activity. Suitable buffers include sodium citrate, ammonium acetate, sodium acetate, disodium phosphate, and any other art recognized buffers.

The term "incubation", as used herein, refers to halting the application of the cellulase solution to the cellulosic-containing fabric and holding the cellulosic-containing fabric with the cellulase solution applied at an elevated temperature (i.e., about 20° C. to about 65° C.) for a period of time from about 1 to 16 hours.

The term "feel" (also referred to as "hand") as used herein refers to the physical smoothness of a cellulosic-containing fabric to touch. Fabrics having improved feel are smoother and silkier to the touch than other fabrics and accordingly are viewed as higher quality products. As defined, the term feel is distinguished from qualities such as softness (which refers to the pliability of the fabric rather than its feel), thickness, color or other physical characteristics not involved in smoothness of the fabric. Such qualities (e.g. softness) can be achieved by treating a cotton woven fabric with a cellulase solution under agitating conditions.

The term "appearance" as used herein refers to the physical appearance of the cellulosic-containing fabric to the eye and is determined in part, by the presence or absence of fuzz, surface fibers, and the like on the surface of the fabric as well as by the ability or inability to discern the construction (weave) of the fabric. Fabrics which have little if any fuzz in surface fibers and wherein the construction (weave) is clearly discernible possess improved appearance as compared to fabrics having fuzz and/or loose fibers and/or an indiscernible weave. Perceived color is affected in the same way as the perceived construction. If the fabric is fuzzy, the fabric appears lighter in color. If the fabric has less fuzz, it appears brighter or richer in color.

The term "contacting under pressure" as used herein refers to applying the cellulase solution to the fabric in conjunction with pressure. Methods of "contacting under pressure" with a cellulase solution include such methods as spraying the cellulose solution onto the fabric or soaking the fabric with the cellulase solution and then passing the fabric through or under a roller to produce a flooding or washing effect in the fabric as the cellulase solution is pushed along the fabric. However, the methods of "contacting under pressure" are not restricted to these methods.

In general, the improvement in feel and appearance in cellulosic-containing fabrics after treatment by the methods of the present invention are readily ascertained by simple analytical tests which provide a numerical rating to the fabric both before and after treatment by the methods of this invention. The test procedure is conducted as a side-by-side comparison of a sample of fabric after treatment by the process of this invention with a fabric sample before treatment or with a standard.

One such analytic test is provided in U.S. Pat. No. 5,232,851, which is incorporated herein by reference in its entirety, which provides a test for cotton woven fabric. However, one skilled in the art could readily extrapolate from cotton woven fabric to cotton knits or cotton denims by substituting cotton knit fabric or cotton denim fabric as the standards.

The analytical test for appearance of cotton woven fabrics described in U.S. Pat. No. 5,232, 851 utilizes the two fabric samples (unlabelled), i.e., one before treatment, one after treatment by the process of this invention, and two standards. The fabrics are visually evaluated for appearance and rated on a 1 to 10 scale by a minimum of seven individuals. The rating assigned to each fabric is based on appearance qualities such as the presence or absence of fuzz and/or loose fibers and/or a discernible weave. The scale has two standards to allow meaningful comparisons. The first standard is a test fabric of cotton sheeting (Style No. 467) available from Testfabrics, Inc. (200 Blackford Avenue, Middlesex, N.J. 08846) which for the purposes of this analysis is assigned an appearance rating of 3. The second standard is a test fabric of mercerized combed cotton broadcloth (Style No. 419) available from Testfabrics, Inc. (200 Blackford Avenue, Middlesex, N.J. 08846) which for the purposes of this analysis is assigned an appearance rating of 7.

The fabric to be rated is provided a rating of 3 or 7 if the fabric appears substantially the same as the first or second standard respectively. A rating of 1–2 represents fabrics having incrementally poorer appearances than the first standard; ratings of 8–10 represent fabrics having incrementally better appearances than the second standard; and ratings of 4–6 represent fabrics having incrementally better appearances than the first standard but incrementally poorer appearances than the second standard. After complete analysis of the two fabrics, the values assigned to each fabric by all of the individuals are added and an average value generated. Fabrics treated by the process of this invention are defined as having an improved appearance if the average value assigned to that fabric is at least 0.5 greater, and preferably at least 1 number greater, than the average value assigned to that fabric prior to treatment.

In U.S. Pat. No. 5,232,851, after the two fabrics have been rated for appearance, the fabrics are then rated for feel. The analytical test for feel utilizes the two fabric samples (unlabelled), one before treatment and one after treatment by the process of this invention. The fabrics are manually evaluated for feel and rated on a 1–10 scale by a minimum of seven individuals. The rating assigned to each fabric is based on feel qualities such as smoothness and silkiness. The scale has two standards to allow meaningful comparisons. The first standard is a test fabric of cotton twill (Style No. 471) available from Testfabrics, Inc. (200 Blackford Avenue, Middlesex, N.J. 08846) which for the purposes of this analysis is assigned a rating of 3. The second standard is a test fabric of mercerized combed cotton broadcloth (Style No. 419) available from Testfabrics, Inc. (200 Blackford Avenue, Middlesex, N.J. 08846) which for the purposes of this analysis is assigned a rating of 7.

The fabric to be rated is given a rating of 3 or 7 if the fabric feels substantially the same as the first or second standard, respectively. Ratings of 1–2 represent fabrics having incrementally poorer feel than the first standard; ratings of 8–10 represent fabrics having incrementally better feel than the second standard; and ratings of 4–6 represent fabrics having incrementally better feel than the first standard but incrementally poorer feel than the second standard. After complete analysis of the two fabrics, the values assigned to each fabric are added and an average value generated. Fabrics treated by the process of this invention are defined as having an improved feel if the average value assigned to that fabric is at least 0.5 greater, and preferably at least 1 greater, than the average value assigned to that fabric prior to treatment.

Another analytical test for appearance and feel can be used. Specifically, the fabric (unmarked) to be rated for feel and appearance is inspected by five (5) individuals. The fabric is visually evaluated for appearance. The individuals are instructed prior to testing that the term "appearance" refers to the physical appearance of the cotton woven fabric to the eye and is determined in part, by the presence or absence of fuzz, surface fibers, and the like on the surface of the fabric as well as by the ability or inability to discern the construction (weave) of the fabric. Fabrics which have little if any fuzz and surface fibers and wherein the construction (weave) is clearly discernable possess improved appearance as compared to fabrics having fuzz and/or loose fibers and/or indiscernible weave. Accordingly, the rating assigned to each fabric is based on appearance qualities such as the presence or absence of fuzz and/or loose fibers and/or a discernible weave.

An untreated sample is used as the standard. A rating of 5 is given to the untreated sample for appearance. A rating of greater than 5 can be given to a treated sample if the treated sample appears worse than the untreated sample. The fabric to be rated is given a rating of 5 if the fabric appears substantially the same as the untreated sample. Ratings of 1–4 represent fabrics having incrementally better appearances than the untreated sample. After complete analysis of the fabrics, the values assigned to each fabric by all of the individuals are added and an average value generated.

The fabrics are also evaluated for "feel". The individuals were instructed prior to testing that the term "feel" (or hand) referred to the physical smoothness of a cotton woven fabric to touch. Fabrics having improved feel are smoother and silkier to the touch than other fabrics and are distinguished from qualities such as softness (which refers to the pliability of the fabric rather than its feel), thickness, color, or other physical characteristics not involved in smoothness of the fabric. The fabrics are manually evaluated for feel by five (5) individuals. The rating assigned to each fabric is based on feel qualities such as smoothness and silkiness, as defined above.

An untreated sample is used as the standard. A rating of 5 is given to the untreated sample for the feel. A rating of greater than 5 can be given to a treated sample if the treated sample feels worse than the untreated sample. The fabric to be rated is given a rating of 5 if the fabric feels substantially the same as the untreated sample. Ratings of 1–4 represent fabrics having incrementally better feel than the untreated sample. After complete analysis of the two fabrics, the values assigned to each fabric are added and an average value generated.

2. Methodology.

In one embodiment of the present invention, the cellulase solution is sprayed into the front and back sides of the fabric from spray bars attached to a reservoir of cellulase solution. The spraying is done at variable pump pressures with variable sizes and numbers of nozzles or slits in the spray bars. All of these variables allow the present invention to be customized for different applications of the cellulase solution to create different feels and appearances on selected fabrics and to be adapted for use on existing cotton fabric aqueous processing machines.

The pressure used during spraying depends on several factors, including but not limited to: thickness of the fabric; size of the slits or apertures in the spray bars; number of spray bars; number of slits or apertures; distance the spray bars are located from the surface of the fabric; configuration of the fabric aqueous processing apparatus; the feel and appearance characteristics desired; rate at which the fabric is moved; concentration of the cellulase in the cellulase solution; etc. The particular pressure employed is selected relative to these factors and it is well within the skill of the art to make this selection.

The methods of applying cellulase solution directly to the fabric under pressure provides several advantages over the methods heretofore employed. Specifically, in art known applications of cellulase, such as, passing fabric through a cellulase solution in a trough or bowl, only about 5–10% of the cellulase molecules adhere to the cellulosic-containing fabric. Without being limited to any theory, it is believed that the cellulase molecules only in the area adjacent to the fabric will contact and then adhere to the fabric since such contact is believed to be controlled, at least in part, by diffusion.

Contrarily, and again without being limited to any theory, it is believed that the contacting under pressure of the present invention allows the cellulase solution to efficiently contact the fabric without any diffusion limitation. Moreover, contacting under pressure is also believed to result in effective penetration of the cellulase into the fabric; to also result in an acceleration of the cascading effect, and to result in a more even coverage of the fabric with cellulase. Again, without being limited to any theory, it is also believed that the pressurized spraying also acts to flush loose fibers out of the fabric and enhances the cascading effect over the cotton fabric. The direct application of the cellulase under pressure described above results in improved feel and appearance characteristics as compared to the fabric prior to treatment, which improvement is achieved in an efficient manner.

It has also been discovered that previously disclosed methods of treating cotton woven fabrics by cascading and/or agitating a cellulase solution over the fabric suffer from the additional drawback that high concentrations of cellulase are required to achieve the desired effect. Without being limited to any theory, it is believed that with the previously disclosed methods, contact of cellulase with the fabric was controlled, at least in part, by diffusion and, accordingly, there is less probability of the enzyme molecules contacting the cellulosic-containing fibers as the fabric moves through the cellulase solution. Without being limited to any theory, it is believed that the direct application of cellulase solution under pressure not only enhances and/or accelerates the cascading effect of the present invention by more efficiently contacting the fabric with the cellulase enzyme, which results in faster treatment times of the fabric and for a reduction in the strength loss, but also permits the use of lower concentrations of enzyme. Moreover, in one embodiment, it is contemplated that the cellulase solution may be recirculated through the spray bars from a trough or bath containing the cellulase solution in order to maximize the cellulase effect on the fabric.

The methods of this invention have the further advantage over previously disclosed methods in that after application of the cellulase solution to the cellulosic-containing fabric through a spray bar, the method does not require incubating the fabric after the application at an elevated temperature for a period of time from about 1 to 16 hours.

The spraying application of the cellulase solution can be achieved by employing a spraying apparatus in conjunction with an apparatus such as a jig, or a continuous range, or washer, and the like. A jig is a well known dyeing apparatus found in mills manufacturing cellulosic-containing fabrics and is generally used for the purpose of desizing/scouring fabrics and dyeing fabrics in open-width form. In a jig, a defined length of cellulosic-containing fabric, in its open width position, is maintained on and between two rollers wherein the fabric is passing from one roller which is in the unwinding stage to a second roller which is in the winding stage. Once the unwinding/winding process is completed, the process is reversed so that the previous unwinding roll becomes the winding roll and the previous winding roll becomes the unwinding roll. This process is continuously conducted during the entire cellulase treatment time.

In one preferred embodiment of the present invention, a variable number of sprayers (e.g., spray bars) are placed between the winding and unwinding rolls on the front and back sides of the cellulosic-containing fabric. More preferably, the sprayers are located at a distance of about 1 to 2 inches (2.54 to 5.08 cm) from the surface of the fabric, although not restricted to this range. Four sprayers are located approximately 12 inches (30.48 cm) above the bath surface. Another four sprayers are located approximately 2 inches (5.08 cm) below the bath surface. The cellulase solution is sprayed into the fabric as the cotton woven fabric passes from the unwinding roll to the winding roll.

Preferably, the sprayers are oriented in such a position that the cellulase solution spray strikes the fabric at a 15 to 90 degree angle, and more preferably a 30 to 45 degree angle. The angled orientation creates an enhanced and/or accelerated cascading action on the front and back sides of the fabric, instead of the cellulase solution passing from the front side of the fabric to the back side of the fabric, and vice versa.

The pressure used for the spraying depends on the several factors discussed above. Preferably, the pressure used is about 0.01 to 30 psi ($7.03 \times 10^{-4}$ to 2.11 kg/cm$^2$), more preferably, about 1 to 5 psi ($7.03 \times 10^{-2}$ to $3.52 \times 10^{-1}$ kg/cm$^2$), and most preferably, about 2 to 3 psi ($1.41 \times 10^{-1}$ to $2.11 \times 10^{-1}$ kg/cm$^2$).

In one embodiment, the cellulase solution is applied between the winding and unwinding roll by spraying only. In another embodiment, the cellulase solution is applied between the winding and unwinding roll by spraying in combination with a trough or bowl containing only water. In another embodiment, the cellulase solution is applied by spraying in combination with a trough or bowl containing a cellulose solution located between the two rollers. The rollers are adjusted so that the cellulosic-containing fabric becomes immersed in the cellulase solution or water as it passes from one roller to the other.

The spray application of the cellulase solution is achieved in the jig by continuously rolling and unrolling the cellulosic-containing fabric from the rolls, preferably at a rate of speed between about 40 to 200 yd/min (36.5 to 183 m/min), and more preferably at about 90 yd/min (82.3 m/min) so that at any given time, part of the length of the fabric is moving past the sprayers at this defined rate of speed. The net result of such rolling and unrolling is, over a given period of time, all of the fabric has been sprayed with the cellulase solution except for the very terminal portions found at either end of the fabric—these terminal ends are often composed of leader fabric, i.e., fabric sewn to the terminal portions of the treated fabric and which is not intended to be treated.

A continuous operation apparatus is similar to a jig in that the cellulosic-containing fabric, in its open width position (some continuous operation units are set up for rope processing of the fabric) is passed through the unit. However, the continuous operation apparatus operates in only one direction and the length of time the fabric is exposed to the cellulase solution can be varied by modifying the rate at which the fabric is moved through the unit, by modifying the unit so as to contain more than one trough and by varying the number of spray bars used.

It is also contemplated that the method of this invention may be employed in conjunction with cascading the enzyme solution across and/or down the fabric. As used herein, the term "cascading" means the rapid flow of cellulase solution across and/or down and eventually away from the surface of the cellulosic-containing fabric. That is to say that cascading occurs when a stream of cellulase solution (liquid) is moving on and relative to at least part of the surface of the cotton woven fabric and this stream eventually moves away from this part of the surface of the fabric. A cascading effect can be achieved, for example, by use of a jig or a continuous operation apparatus.

For example, as described in U.S. Pat. No. 5,232,851, when a jig is employed the cellulosic-containing fabric rapidly departs from the trough containing the cellulase solution and is lifted somewhat upward in order to be wound onto the winding roller. When this occurs, any cellulase solution found on the surface of the cellulosic-containing fabric as the fabric is raised upward rapidly flows down and/or across and eventually off this part of the fabric surface. Specifically, cascading in a jig is achieved by the passage of the cellulosic-containing fabric through the cellulase solution, preferably at a speed in the range of 40 yd/min (36.6 m/min) to 200 yd/min (182.9 m/min), and more preferably at a speed of about 90 yd/min (82.2 m/min), coupled with the gravitational effect of the upward lift of the fabric as it is being rolled which results in the rapid flow of the cellulase solution down and/or across and eventually away from the surface of the cellulosic-containing fabric, theretofore covered with the cellulase solution. It is contemplated that the squeezing action as the wet fabric rolls up on the winding roll also causes the cellulase solution to cascade across and/or down the fabric surface.

Without being limited to any theory, it is believed that cascading is enhanced and/or accelerated by the use of the sprayers during the cascading process. Specifically, it is believed that the pressurized spray forces the cellulase solution to move on and along the length of at least part of the surface of the cellulosic-containing fabric either prior to entry into the cellulase solution containing trough or as it exits from the cellulase solution containing trough.

One of ordinary skill in the art can select a pressure sufficient enough to accomplish the enhanced and/or accelerated cascading effect based on the factors discussed above. It is believed that this enhanced and/or accelerated cascading also operates to flush out loose fibers on the surface of the cellulosic-containing fabric.

Without being limited to any theory, it is believed that when the cellulase solution is applied directly onto the cellulosic-containing fabric, the cellulase enzyme comes in contact with the fabric at a much higher rate than just passing the fabric through a cellulase solution. In other words, the cellulase molecules have a higher probability of contacting and adhering to the surface of the fabric when directly applied under pressure, than when the fabric is passed continuously through a bath. In the latter case, only a small percent of the cellulase molecules in the solution contact the fabric as it passes through the bath, which leaves a deficit of cellulase molecules next to the fabric surface. This deficit is mitigated by cellulose molecules that migrate by diffusion from an area of the bath that is away from the fabric surface. However, diffusion is not an efficient process and long contact times or higher cellulase concentrations may be required to achieve the desired enhancements in feel and appearance.

With the methods of the present invention, the reaction time required to achieve the desired improvements in feel and appearance in the cellulosic-containing fabric is unexpectedly reduced. Without being limited to any theory, it is believed that this reduction in reaction time is achieved by more efficient contact of the cellulase molecules with the fabric by direct application of the cellulase solution to the fabric under pressure.

Because of this reduction in reaction time, the cellulosic-containing fabric is exposed to the cellulase solution for shorter periods of time which results in less strength loss from cellulase exposure. The result is that with all factors being equal, (e.g., reaction temperature, cellulase concentration, buffer concentration, etc.), the direct application of cellulase under pressure during the enzyme treatment results in substantially shorter reaction times for exposure of the cellulosic-containing fabric to the cellulase solution as compared to the reaction time required for cellulase treatment without spraying. Additionally, and as noted above, the direct application of cellulase solution under pressure to the cellulosic-containing fabric results in improvements in the feel and appearance of the so-treated fabric with a reduction in the strength loss.

The tensile strength of cellulosic-containing fabrics is generally measured in a warp and filling direction which are at right angles to each other. Accordingly, the term "warp tensile strength" as used herein refers to the tensile strength of the cellulosic-containing fabric as measured along the length of the cellulosic-containing fabric, whereas the term "filling tensile strength" refers to the tensile strength of the cellulosic-containing fabric as measured across the width of the cellulosic-containing fabric. The tensile strength of the resulting cellulosic-containing fabric treated with a cellulase solution is compared to its tensile strength prior to treatment with the cellulase solution so as to determine the fabric strength loss resulting from the treatment. If the tensile strength is reduced too much, the resulting cellulosic-containing fabric will easily tear and/or form holes. Accordingly, it is desirable to maintain a tensile strength (both warp and filling) after treatment which is at least about 35% of the tensile strength before treatment, and more preferably 60% of the tensile strength before treatment.

The tensile strength of cellulosic-containing fabrics is readily conducted following ASTM D1682 test methodology. Equipment suitable for testing the tensile strength of such fabrics include a Scott tester (Industrial Equipment Co., Charlotte, N.C.), or an Instron tester (Instron Corp., Atlanta, Ga.), both of which are commercially available. In testing the tensile strength of cellulosic-containing fabrics which have been treated with cellulose solutions, care should be taken to prevent fabric shrinkage after treatment and before testing for more accurate tensile strength data.

The tear strength of cellulosic-containing fabrics is readily conducted following ASTM D2261 test methodology. Equipment suitable for testing the tear strength of such fabrics include a Scott tester (Industrial Equipment Co., Charlotte, N.C.), or an Instron tester (Instron Corp., Atlanta, Ga.), both of which are commercially available. In testing the tear strength of cellulosic-containing fabrics which have been treated with cellulase solutions, care should be taken to prevent fabric shrinkage after treatment and before testing for more accurate tear strength data.

The cellulosic-containing fabrics treated by the methods herein described possess warp tensile strength values which are at least about 35% of the warp tensile strength values of the fabric prior to treatment; preferably, at least about 60% of the warp tensile strength values of the fabric prior to treatment; and more preferably, at least about 80% of the warp tensile strength values of the fabric prior to treatment.

The cellulosic-containing fabrics treated by the methods herein described possess filling tensile strength values which are at least about 35% of the filling tensile strength values of the fabric prior to treatment; preferably, at least about 60% of the filling tensile strength values of the fabric prior to treatment; and more preferably, at least about 80% of the filling tensile strength values of the fabric prior to treatment.

In addition to improving the feel and appearance of cellulosic-containing fabrics, it has been found that the methods of the present invention additionally result in the removal of immature cellulosic-containing fibers from the fabric. For the purposes of this application, the term "immature cellulosic-containing fibers" means cellulosic-containing fiber which has not grown to maturity. Immature cellulosic-containing fibers will dye lighter than mature cellulosic-containing fibers which results in undesirable specks on the fabric when the immature cellulosic-containing fiber is incorporated into yarn and, in turn, into fabric. As noted above, cellulase treatment in accordance with the methods of this invention removes a portion of the immature cellulosic-containing fiber. This results in improved uniformity of the dye shade when the fabric is dyed which, in turn, imparts higher quality to the fabric. It is contemplated that, the cellulase treatment can also be applied after dyeing, as required.

For the present invention, the number of spray bars or sprayers, the number of nozzles or slits, and the slit size in the spray bar, the pump pressure, etc. employed herein is dependent on factors such as the configuration of the jig or continuous operating apparatus to be used, the feel and appearance characteristics desired, the rate at which the fabric is passed through the machine, the concentration of the cellulase solution, etc. A person, generally, skilled in the art knows how to balance all the factors to select the proper configuration.

Following are examples of possible configurations, but a person skilled in the art will recognize that these factors are not confined to these ranges. The number of spray bars required is generally between 1 and 50. More preferably, between 1 and 20. The slit size in the spray bar is preferably in the range of 0.025 to 0.050 inches (0.0635 to 0.127 cm) wide, more preferably, 0.0375 inches (0.095 cm) wide.

The pump pressure should be sufficient to produce the flooding and cascading effect without causing the cellulase solution to pass from the front side of the fabric to the back side of the fabric, and vice versa. The pump pressure can be readily determined by the skilled artisan based on this consideration, the factors discussed above, and the desired effect. Preferably, the pressure used is about 0.01 to 30 psi ($7.03 \times 10^{-3}$ to 2.11 kg/cm$^2$), more preferably, about 1 to 5 psi ($7.03 \times 10^{-3}$ to $3.52 \times 10^{-1}$ kg/cm$^2$), and most preferably, about 2 to 3 psi ($1.41 \times 10^{-1}$ to $2.11 \times 10^{-1}$ kg/cm$^2$).

The aqueous cellulase solution contains cellulase and other optional ingredients including, for example, a buffer, a scouring and/or wetting agent, and the like. The concentration of cellulase employed in this solution is generally a concentration sufficient for its intended purpose. That is to say that an amount of cellulase is employed to provide improved feel and appearance. The amount of cellulase employed is also dependent on the spraying equipment employed, the process parameters employed (e.g., the speed of the fabric in a jig, the temperature of the cellulase solution, and the like), the exposure time to the cellulase solution, cellulase activity (e.g., the method of this invention will require a cellulase solution having a lower concentration of a more active cellulase system as compared to a less active cellulase system), and the like. The exact concentration of cellulase can be readily determined by the skilled artisan based on the above factors as well as the desired effect.

Preferably, the concentration of the cellulase and the cellulase solution employed herein is from about 0.25 grams/liter to about 8 grams/liter ($2.09 \times 10^{-3}$ to $6.68 \times 10^{-2}$ lbs/gal) of cellulase solution, and more preferably, from about 2 grams/liter to about 6 grams/liter ($1.67 \times 10^{-2}$ to $5.01 \times 10^{-2}$ lbs/gal) of cellulase solution. (The cellulase concentration recited above refers to the total weight of the commercial enzyme per liter of liquid).

When a buffer is employed in the cellulase solution, the concentration of buffer in the aqueous cellulase solution is that which is sufficient to maintain the pH of the solution within the range wherein the employed cellulase exhibits activity which, in turn, depends on the cellulase employed. The exact concentration of buffer employed will depend on several factors which the skilled artisan can readily take into account. For example, in a preferred embodiment, the buffer as well as the buffer concentration are selected so as to maintain the pH of the cellulase solution within the pH range required for optimal cellulose activity.

In general, buffer concentration in the cellulase solution is about 0.005 N and greater. Preferably, the concentration of the buffer in the cellulase solution is from about 0.01 to about 0.5 N, and more preferably, from about 0.05 to about 0.15 N. In general, increased buffer concentrations in the cellulase solution are believed to enhance the rate of tensile strength loss of the treated fabric.

Reaction temperatures for cellulase treatment are governed by two competing factors. Firstly, higher temperatures generally correspond to enhanced reaction kinetics, i.e., faster reactions, which permit reduced reaction times as compared to reaction times required at lower temperatures. Accordingly, reaction temperatures are generally at least about 30° C. and greater. Secondly, cellulase is a protein which denatures at higher reaction temperatures. Thus, if the reaction temperature is permitted to go too high, then the cellulolytic activity is lost as a result of the denaturing of the cellulase. As a result, the maximum reaction temperatures employed herein are generally about 60° C. In view of the above, reaction temperatures are generally from about 30° C. to about 60° C.; and preferably, from about 35° C. to about 57° C., and more preferably, from about 50° C. to about 57° C.

As a result of the spray treatment, the range of reaction time required to achieve improved feel and appearance in the cellulosic-containing fabric is substantially shorter than those ranges previously employed without the spray apparatus. While the exact length of reaction time employed herein is dependent on factors such as the temperature of the cellulase solution, the concentration of the cellulase in the solution, etc., in a preferred embodiment improved feel and appearance in cellulosic-containing fabric can be achieved by the methods described herein within a reaction time of from about 0.5 to about 3 hours.

In a preferred embodiment, a concentrate can be prepared for use in the methods described herein. Such concentrates would contain concentrated amounts of cellulase, buffer and surfactant, preferably in an aqueous solution. When so formulated, the concentrate can readily be added to water so as to quickly and accurately prepare cellulase solutions having the requisite concentration of these additives. As is readily apparent, such concentrates will permit facile formulation of the cellulase solutions as well as permit feasible transportation of the concentration to the location where it will be used.

It is further contemplated that other methods of applying the cellulase solution to the fabric may result in the benefits observed with the methods of this invention. For example in one embodiment, the cellulase solution may be present in the fabric as the fabric is squeezed between or under a roller, a sponge, a brush, or a bar.

It is contemplated that the method of the present invention could be used to apply solutions containing lipases, such as those disclosed in U.S. Pat. Nos. 4,981,611 and 3,950,277, and British Specification No. 1,372,034, the disclosures of which are incorporated herein by reference, to polyester fabrics or to apply solutions containing proteases, such as "PURIFACT" (available from Genencor International, South San Francisco, Calif.) and "SAVINASE" (available from NOVO Industry, Copenhagen, Denmark), or such as those disclosed in U.S. Pat. Nos. 4,760,025 and 5,185,258, and pending U.S. application Ser. No. 08/137,240 filed Oct. 14, 1993 and pending U.S. application Ser. No. 07/950,856 filed Sep. 24, 1992, the disclosures of which are incorporated herein by reference, to silk or wool.

The following examples are offered to illustrate the present invention and should not be construed in any way as limiting its scope.

EXAMPLES

Example 1

Sheeting fabric (cotton/polyester blend) was treated by using a jig. The cellulase solution employed in this example contained 4 grams/liter (0.033 lbs/gal) of "PRIMAFAST 100" cellulase (available from Genencor International, South San Francisco, Calif.), 3.8 grams/liter (0.032 lbs/gal) acetic acid (56%), and 1.9 grams/liter (0.016 lbs/gal) NaOH (50%).

Prior to treatment of the sample, the pH of the cellulase solution was adjusted to 4.5–5.0 and the temperature of the solution was set and maintained at 135° F. (58° C.) throughout the treatment period.

Eight spray bars were used with slit width sizes of 0.050 inches (0.127 cm). The pump pressure was maintained between 2–3 psi (0.14 to 0.21 kg/cm$^2$) to apply the cellulase solution to the sheeting fabric through the slits in the spray bar. Four spray bars were located above the cellulase solution level contained in a trough. Two of those spray bars were located on the front side of the fabric and two on the backside of the fabric. The other four spray bars were located below the cellulase solution level contained in the trough. Two of those spray bars were located on the front side of the fabric and two on the backside of the fabric.

The jig speed was set at 45 yds/min (41.15 m/min) for both trials. In the first trial, the fabric was run through the jig for 30 minutes. The fabric was then removed and the warp tear (lbs.), fill tear (lbs.) and fiber content were determined.

In the second trial, the fabric was run through the jig for 1 hour. The fabric was then removed and the warp tear (lbs.), fill tear (lbs.) and fiber content were determined. A control sample of untreated fabric was also tested for the above qualities.

The results of these determinations are set forth in Table I below. In general, both treated test fabrics showed excellent removal of dead and immature cotton, as well as surface cleanup. Normally, without the spray bars, it would take 2–3 hours to achieve the same results with a drastic decrease in tear strength.

TABLE I

| Fabric Sample | Tear (lbs) | | Fiber Content[b] (%) | |
|---|---|---|---|---|
| | Warp | Fill | Cotton | Polyester |
| Control, untreated | 1.8 | 1.8 | 57 | 43 |
| Treated, 30 min. | 2.1[a] | 2.0[a] | 56 | 44 |
| Treated, 1 hr | 1.8 | 1.3 | 56 | 44 |

[a]The values for the 30 minute treatment time were higher because of shrinkage. However, the values for the untreated control sample and 30 minute treatment time sample are statistically equivalent when the shrinkage is factored out.
[b]The change in the percentage of the fiber content is statistically negligible.

EXAMPLE 2

Nine samples of 100% cotton tablecloth material were treated by using a jig. The cellulase solution employed, the number of spray bars employed, and the length of treatment time were changed for different samples.

For samples 1–4, 7, and 8, the cellulase solution contained 4 grams/liter (0.033 lbs/gal) of "PRIMAFAST 100" cellulase (available from Genencor International, South San Francisco, Calif.), 3.8 grams/liter (0.032 lbs/gal) acetic acid (56%), and 1.9 grams/liter (0.016 lbs/gal) NaOH (50%). For samples 5, 6, and 9 the cellulase solution contained 8 grams/liter (0.067 lbs/gal) of "PRIMAFAST 100" cellulase (available from Genencor International, South San Francisco, Calif.), 3.8 grams/liter (0.032 lbs/gal) acetic acid (56%) and 1.9 grams/liter (0.016 lbs/gal) NaOH (50%).

Prior to treatment of the samples, the pH of the cellulase solution was adjusted to 4.5–5.0 and the temperature of the solution was set and maintained at 135° F. (58° C.) throughout the treatment period.

Eight spray bars were used for this example. Four spray bars were located above the cellulase solution level contained in a trough. Two of those spray bars were located on the front side of the fabric and two on the backside of the fabric. The other four spray bars were located below the cellulase solution level contained in the trough. Two of those spray bars were located on the front side of the fabric and two on the backside of the fabric.

The four spray bars above the cellulase solution level had 0.025 inch (0.0635 cm) slits and the pump pressure was maintained at 5 psi (0.35 kg/cm$^2$). The four spray bars located below the cellulase solution level had 0.050 inch (0.127 cm) slits and the pump pressure was maintained at 2 psi (0.14 kg/cm$^2$).

Sample 0 was maintained untreated as a control sample. Sample 1 was treated by the prior art method of merely passing the sample through the cellulase solution contained in the trough without the aid of the spray bars. For samples 2–6 and 9, only the spray bars above the cellulase solution level were used. For sample 7, all spray bars were used. For sample 8, only the spray bars below the cellulase solution level were used.

The jig speed was set at 45 yds/min (41.15 m/min) for all trials. For trial 1, the fabric was run through the jig for 120 minutes in the prior art manner with no spray bars, just a trough of cellulase solution. For trials 2 & 9, the fabric was run through the jig for 60 minutes. For trials 3, 6, 7 and 8, the fabric was run through the jig for 30 minutes. For trials 4 & 5, the fabric was run through the jig for 15 minutes.

At the end of each treatment period, the fabric was removed from the jig for determining the warp tear strength loss (%), fill tear strength loss (%), the warp tensile strength loss (%), the fill tensile strength loss (%), the appearance and the feel. The control sample was also tested for appearance and feel.

Specifically, the fabrics (unmarked) to be rated for feel and appearance were inspected by five (5) individuals. The fabrics were visually evaluated for appearance and rated on a 1 to 5 scale. The individuals were instructed prior to testing that the term "appearance" referred to the physical appearance of the cotton woven fabric to the eye and is determined in part, by the presence or absence of fuzz, surface fibers, and the like on the surface of the fabric as well as by the ability or inability to discern the construction (weave) of the fabric. Fabrics which have little if any fuzz and surface fibers and wherein the construction (weave) is clearly discernable possess improved appearance as compared to fabrics having fuzz and/or loose fibers and/or indiscernible weave. Accordingly, the rating assigned to each fabric is based on appearance qualities such as the presence or absence of fuzz and/or loose fibers and/or a discernible weave.

Sample 0 (the untreated sample) was used as the standard. A rating of 5 was given to the untreated sample for appearance. The fabric to be rated was provided a rating of 5 if the fabric appeared substantially the same as the untreated sample. Ratings of 1–4 represent fabrics having incrementally better appearances than the untreated sample. After complete analysis of the fabrics, the values assigned to each fabric by all of the individuals were added and an average value generated.

The fabrics were also manually evaluated for "feel" and rated on a 1 to 5 scale. The individuals were instructed prior to testing that the term "feel" (or hand) referred to the physical smoothness of a cotton woven fabric to touch. Fabrics having improved feel are smoother and silkier to the touch than other fabrics and are distinguished from qualities such as softness (which refers to the pliability of the fabric rather than its feel), thickness, color, or other physical characteristics not involved in smoothness of the fabric. The fabrics were manually evaluated for feel and rated on the 1 to 5 scale by five (5) individuals. The rating assigned to each fabric is based on feel qualities such as smoothness and silkiness, as defined above.

Sample 0 (the untreated sample) was used as the standard. A rating of 5 was given to the untreated sample for the feel. The fabric to be rated was given a rating of 5 if the fabric felt substantially the same as the untreated sample. Ratings of 1–4 represent fabrics having incrementally better feel than the untreated sample. After complete analysis of the two fabrics, the values assigned to each fabric were added and an average value generated.

The results of the tests for tensile strength loss, tear strength loss, appearance and feel appear in Table II.

TABLE II

| Fabric Sample | Cellulase Concentration[a] | Treatment Time (min.) | Spray Bars Top | Spray Bars Bottom | Tensile Loss[b] (%) Warp | Tensile Loss[b] (%) Fill | Tear Loss[b] (%) Warp | Tear Loss[b] (%) Fill | Appearance[c,d] | Feel[c] |
|---|---|---|---|---|---|---|---|---|---|---|
| 0 | — | — | — | — | — | — | — | — | 5 | 5 |
| 1 | 4 | 120 | no | no | 20 | 55 | 20 | 40 | 3 | 3 |
| 2 | 4 | 60 | yes | no | 20 | 65 | 10 | 40 | 1 | 1 |
| 3 | 4 | 30 | yes | no | 10 | 20 | 0 | 20 | 1 | 1 |
| 4 | 4 | 15 | Yes | no | 10 | 30 | 0 | 25 | 2 | 1 |
| 5 | 8 | 15 | yes | no | 10 | 25 | 0 | 25 | 2 | I |
| 6 | 8 | 30 | yes | no | 15 | 30 | 0 | 25 | 1 | 1 |
| 7 | 4 | 30 | yes | yes | 15 | 40 | 15 | 30 | 1 | 1 |
| 8 | 4 | 30 | no | yes | 10 | 30 | 10 | 20 | 1 | 1 |
| 9 | 8 | 60 | yes | no | 20 | 50 | 40 | 45 | 1 | 1 |

[a]"PRIMAFAST 100" (grams/liter)
[b]Percentage loss in tensile and tear strength was rounded off to the nearest 5% multiple
[c]1 = best, 5 = worst.
[d]Appearance is rated on the degree of fuzziness and surface cleanup (i.e. rips, fabric irregularities.)

The above data indicates that 4 grams/liter (0.033 lbs/gal) "PRIMAFAST 100" cellulase (available from Genencor International, South San Francisco, Calif.) was adequate to obtain improved feel and appearance. A treatment time of 30 minutes appeared to provide fabric improvements with minimal strength loss. A treatment time of 30 minutes is a significant improvement over the prior art treatment time of 120 minutes illustrated by Sample 1. The data also illustrates that 4 spray bars all located above the cellulase solution level contained in the trough were adequate for achieving the desired improvements in feel, appearance, and reduction in treatment time.

By following the procedures set forth in Examples 1 and 2 above, other cellulases, including cellulase derived from organisms other than *T. longibrachiatum*, could be employed merely by substituting for "PRIMAFAST 100" cellulase (available from Genencor International, South San Francisco, Calif.). Other suitable cellulases which are commercially available and which could be employed herein include "CELLUCLAST" (available from NOVO Industry, Copenhagen, Denmark), "RAPIDASE" (available from Gist Brocades, N.V., Delft, Holland), "CYTOLASE 123" (available from Genencor International, South San Francisco, Calif.), and the like.

One skilled in the art using the methods of the present invention could add more sprayers, change the pump pressure, vary the cellulase concentration, etc. to achieve desired effects in feel, appearance, and treatment time.

What is claimed is:

1. A method for improving the feel and appearance of cellulose-containing fabric prior to finishing of said fabric which method comprises:
   contacting the fabric with a cellulase solution under pressure sufficient to produce a flooding effect in the fabric as the cellulase solution is pushed along the fabric, and under conditions wherein the solution cascades across the fabric and under conditions effective in improving the physical smoothness and appearance of the cellulose-containing fabric.

2. The method of claim 1 wherein contacting the cellulose-containing fabric with the cellulase solution under pressure is accomplished in the absence of halting the application of the cellulase solution to the cellulose-containing fabric and holding the cellulose-containing fabric with the cellulase solution applied at an elevated temperature for a period of time from about 1 to 16 hours.

3. The method of claim 1 wherein contacting the cellulose-containing fabric with the cellulase solution under pressure is accomplished in the absence of additional aqueous solution.

4. The method of claim 1 wherein contacting the cellulose-containing fabric with the cellulase solution under pressure is accomplished by moving the fabric continuously past a dispersing means.

5. The method of claim 4 wherein the moving of the cellulose-containing fabric is accomplished by passing a defined length of fabric between one roller which is in the unwinding stage and a second roller which is in the winding stage.

6. The method of claim 5 wherein when the winding process is complete, the process is reversed with the unwinding roller becoming the winding roller.

7. The method of claim 4 wherein the dispersing of the cellulase solution is applied to the cellulosic-containing fabric by spraying the cellulase solution.

8. The method of claim 7 wherein the cellulase solution is sprayed on a 30 to 45 degree angle to the fabric.

9. The method of claim 1 wherein said method also results in the removal of immature cellulose-containing fibers from the cellulosic-containing fabric.

10. A method as described in claim 1 wherein the cellulose-containing fabric is contacted with the cellulase solution for a period of time of from about 0.25 hours to about 3 hours.

11. The method of claim 10 wherein the concentration of cellulase in said cellulase solution is from about 0.25 gram/liter to about 8 gram/liter.

12. The method of claim 11 wherein the concentration of cellulase in said cellulase solution is from about 2 gram/liter to about 6 gram/liter.

13. The method of claim 1 wherein the cellulase solution is applied to a front side and a back side of the fabric.

14. The method of claim 1 wherein the cellulase solution is applied to only one side of the fabric.

15. The method of claim 1 wherein contacting the cellulose-containing fabric with the cellulase solution in conjuction with pressure is accomplished by moving a dispersing means in relation to the fabric.

16. The method of claim 15 wherein the dispersing of the cellulase solution is accomplished by spraying the cellulase solution.

17. The method of claim 16 wherein the cellulase solution is sprayed on a 30 to 45 degree angle to the fabric.

18. The method of claim 1 which further comprises immersing the fabric in an effective amount of cellulase solution.

19. A method for improving the feel and appearance of cellulose-containing fabric prior to finishing of said fabric which method comprises:

contacting the fabric with a cellulase solution under pressure in the range of 0.01 to 30 psi, and under conditions wherein the solution cascades across the fabric and under conditions effective in improving the physical smoothness and appearance of the cellulose-containing fabric.

20. The method of claim 19 wherein contacting the cellulose-containing fabric with the cellulase solution under pressure is accomplished by spraying the cellulase solution.

21. The method of claim 19 wherein contacting the cellulose-containing fabric with the cellulase solution under pressure is sufficient to flush loose fibers out of the fabric.

* * * * *